Jan. 1, 1952 R. S. JOHNSON Plant Pat. 1,064
PLUM TREE
Filed Jan. 13, 1950
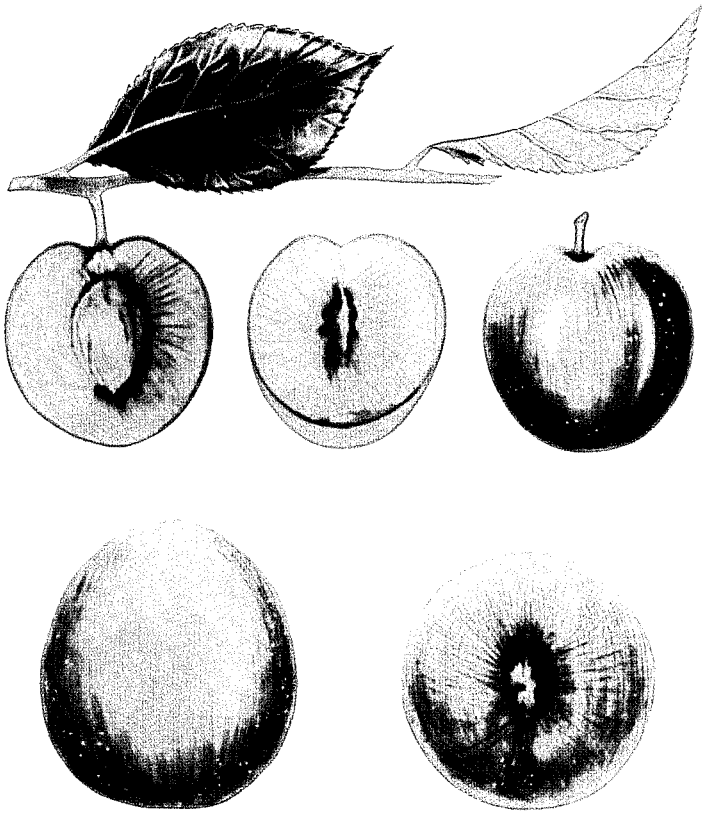
Inventor.
Ruth S. Johnson
By: Robert Cobb
Attorneys Patented Jan. 1, 1952

Plant Pat. 1,064

UNITED STATES PATENT OFFICE 1,064

PLUM TREE

Ruth S. Johnson, Oklahoma City, Okla., assignor to Stark Bro's Nurseries And Orchards Company, Louisiana, Mo., a corporation of Missouri Application January 13, 1950, Serial No. 138,405

1 Claim. (Cl. 47—62)

The present discovery relates to a new and distinct variety of plum tree, originating as a selected seedling that was produced by me from seed which I planted, cultivated, nurtured, observed, tested and asexually reproduced in my cultivated orchard near Oklahoma City, Oklahoma, and which resulted in the creation of a new variety which is primarily characterized by bearing large, attractive, red-skinned, red-fleshed fruit of superior size and quality. It is highly resistant to bacterial leaf spot and canker caused by *Xanthomonas pruni*.

As compared to other red-fleshed plums of similar type, the new variety is an exceptionally heavy producer and much more productive than "Elephant Heart" (unpatented), much more resistant to bacterial canker than "Flaming Delicious" (Plant Patent No. 14) or "Shiro" (unpatented), and the size and quality of the fruit are much superior to those of "Santa Rosa" (unpatented).

These distinctive tree and fruit characteristics represent a marked improvement in plum trees, and said characteristics have been found to be established and fixed by asexual reproduction of the variety by means of budding, at Louisiana, Missouri.

The drawing illustrates specimens of the foliage and of the fruit in both section and elevation.

The following is a detailed description of the new variety, giving color designations according to the conventional dictionary definition of terminology as well as corresponding color terms according to Ridgway's Color Standards and Nomenclature and Horticultural Color Guide (observations were made near Louisiana, Missouri).

Dates first and last picking: August 9th–August 16th.

Tree: Medium size; medium vigorous; open; upright; vase-formed; hardy; productive; regular bearer.

*Trunk.*—Medium slender; medium smooth.

*Branches.*—Medium slender; smooth; dull gray; Light Neutral Gray, Plate LIII tone b (Ridgway). *Lenticles*—numerous; large.

*Leaves.*—Length—3¾ inches; width—1½ inches. Medium size; oval; acutely pointed; medium thick; dark green; Empire Green, Plate XXXII, Color No. 33'', tone m (Ridgway). smooth. Margin—glandular; finely serrate. Petiole—medium length; medium thick. Glands—alternate; medium size; reniform; free; average number, 2.

*Flowers.*—Dates first and full blossom—March 17th–March 23rd. (Ripe July 28th to August 4th.) Early; medium size; white.

Fruit: Maturity when described—eating ripe. Date—August 14th.

*Size.*—Uniform; large. Axial diameter, 2¼ inches. Transverse in suture plane, 2 inches. At right angles to suture plane, $2\frac{1}{16}$ inches.

*Form.*—Uniform; symmetrical; broadly ovoid; compressed transversely toward suture; side unequal. Suture—distinct; extends from base but discontinues at apex. Ventral surface—rounded. Cavity—flaring; circular; suture showing on one side. Depth, $\frac{3}{16}$ inch; breadth, $\frac{7}{16}$ inch. Base—truncate. Apex—rounded. Pistil point—oblique. Stem—medium stout; length ⅝inch; glabrous. Adherence to stone—strong. Skin—medium thin; tough; astringent; tenacious to flesh. Tendency to break—none in wet or dry season. Color—highly blushed red; Indian Lake, Color No. 826/1, page 170, vol. 2 (Horticultural Color Guide). Down—wanting.

*Flesh.* — Color — blood; Chrysanthemum Crimson, Color No. 824/2, page 169, vol. 2, (Horticultural Color Guide).

*Amygdalin.*—Wanting. Juice—abundant; rich.

*Texture.*—Meaty.

*Fibres.*—Few; fine; tender.

*Ripens.*—Fairly even; earliest at apex.

*Flavor.*—Mild; Vinous.

*Aroma.*—Distinct.

*Eating quality.*—Best.

Stone:—Cling; adheres to flesh over entire surface; fibres long.

*Size.*—Small; length 1 inch; thickness $\frac{5}{16}$ inch.

*Form.*—Oval; cuneate toward base and apex.

*Base.*—Straight. Hilum—oval. Apex—acuminate.

*Sides.*—Equal; curved on right and left sides.

*Pits.*—Ventral edge—thin with wing throughout.

*Dorsal edge.* Narrow with shallow, narrow groove throughout. Ridges on either side—continuous.

Use: Market; dessert; canning.

Keeping quality: Good.

Resistance to:

*Insects.*—Medium good.

*Diseases.*—Good.

Shipping quality: Good.

I claim:

A new and distinct variety of plum tree, characterized as to novelty by its exceptionally heavy productivity of large, attractive, red-skinned, red-fleshed fruit of superior size and quality, and by its superior resistance to bacterial leaf spot and canker caused by *Xanthomonas pruni*, substantially as shown and described.

RUTH S. JOHNSON.

REFERENCES CITED

The following references are of record in the file of this patent:

UNITED STATES PATENTS

| Number | Name | Date |
|---|---|---|
| Pl. Pt. 14 | Burbank | Apr. 5, 1932 |
| Pl. Pt. 111 | Thompson | Nov. 13, 1934 |